United States Patent [19]

McCrory et al.

[11] Patent Number: 5,190,529
[45] Date of Patent: Mar. 2, 1993

[54] ADVANCEMENT SLEEVE AND ADAPTER FOR A CATHETER

[75] Inventors: Jennifer J. McCrory, Lincoln, R.I.; James P. Cianci, Walpole, Mass.

[73] Assignee: The Kendall Company

[21] Appl. No.: 703,321

[22] Filed: May 20, 1991

[51] Int. Cl.⁵ .............................................. A61M 5/32
[52] U.S. Cl. .................................. 604/175; 604/264; 604/280
[58] Field of Search ................. 604/103, 158, 163–165, 604/167, 169, 174, 175, 240–243, 256, 264, 265, 280, 283

[56] References Cited

U.S. PATENT DOCUMENTS

| | | | |
|---|---|---|---|
| 4,634,433 | 1/1987 | Osborne | 604/163 |
| 4,911,691 | 3/1990 | Aniuk et al. | 604/164 |
| 4,936,826 | 6/1990 | Amarasinghe | 604/175 |
| 5,059,186 | 10/1991 | Yamamoto et al. | 604/280 |

*Primary Examiner*—John D. Yasko
*Assistant Examiner*—Anthony Gutowski
*Attorney, Agent, or Firm*—Alvin Isaacs

[57] ABSTRACT

Disclosed is an article for use as a component part of a catheter system wherein a proximal section is exteriorized above the skin for connection to a liquid drug source, the article comprising a flexible sleeve having an advancement tip at its distal end to facilitate advancement of the sleeve into a passage beneath the skin created by tunneling the catheter subcutaneously to an exit site where the proximal end is exteriorized, the advancement tip having a generally bullet-shaped leading end and a base section having an outer diameter greater than the outer diameter of the sleeve, the advancement tip having a channel extending therethrough for receiving the catheter for passage through the sleeve; an adapter for placing the proximal end of the catheter in liquid communication with the drug source, the adapter having a channel extending longitudinally between the adapter ends, an opening at the distal end of the adapter communicating with the adapter channel and through which the proximal end of the catheter can be inserted, the proximal end of the catheter is releasably secured within the opening and in liquid communication with the adapter channel, and the proximal end of the sleeve is permanently attached to the distal end of the adapter with the sleeve surrounding the opening in the adapter so that a catheter extending through the sleeve may be introduced into the adapter opening to receive liquid drug passing therethrough.

22 Claims, 4 Drawing Sheets

ADVANCEMENT SLEEVE AND ADAPTER FOR A CATHETER

BACKGROUND OF THE INVENTION

This invention relates to long-term epidural catheters adapted for use in pain management, e.g. to relieve intractable pain in cancer patients.

Heretofore, a number of different methods have been utilized to relieve intractable pain. These include palliative or "curative" therapy (i.e. surgery, radiation therapy or chemotherapy), systemically administered narcotics, transcutaneous electrical stimulation, nerve blocks, rhizotomy, radiofrequency, induced lesions, epidural or dorsal column electrical stimulation, and central nervous system neurosurgical intervention, e.g. cordotomy, thalamotomy, acupuncture, and hypnosis.

While systems for relieving cancer pain by the administration of morphine using an indwelling system have been disclosed in the literature for some time, e.g. in "Cancer Pain Relieved by Long-Term Epidural Morphine With Permanent Indwelling Systems for Self-Administration", by C. Poletti et al, *Journal of Neurosurgery*, Vol. 55, October, 1981, pp 581-584, it has only been relatively recently that the treatment of intractable pain by epidural infusion of a narcotic has gained acceptance in a number of medical centers.

More recently, the responsibility for the treatment and control of pain has been moving from the surgeon and general practitioner to the anesthesiologist. As anesthesiologists are broadening their practice outside the operating room suite, they are managing acute pain in the post-operative areas and chronic pain in the clinics.

In the past five years, approximately one thousand pain clinics have been established, about 60% of which are headed by anesthesiologists. A majority of these pain clinics treat cancer pain and many are affiliated with a cancer treatment center.

One of the treatment modalities gaining in popularity for terminal cancer pain management is the tunneled epidural catheter. This procedure provides better analgesia without frequent injections or cumbersome I.V. equipment, present fewer complications, and are generally better tolerated by the patient. Epidural narcotic administration works well because there are opiate receptors located all along the spinal cord. Thus, the narcotic can act directly on the receptors, producing localized analgesia without more blockage. This in turn allows for lower dosages and minimizes cerebral and systemic effects.

The tunneled epidural catheters currently on the market are what may be termed a "two-piece" catheter consisting of a first or distal piece for introduction into the epidural space, e.g. as close to the dorsal midline as possible, and a second or proximal piece which is tunneled subcutaneously between the dorsal paravertebral entry site of the first piece and a lateral or ventral exit site from the skin where it is to be connected to a syringe or other source of the narcotic to be administered for pain management.

The tunneling may be effected in the direction from the exit site to the first catheter piece or, alternatively, it may be the reverse, namely from the first catheter piece to the exit site. In either case, the proximal end of the first or distal piece is secured in fluid-tight relationship to the distal end of the second or distal catheter piece and sutured in place to provide a tunneled long-term epidural catheter extending from the dorsal point where it is introduced into the epidural space to a desired location on the side or front of the patient for more comfortable and accessible hook-up to a source of the narcotic to be administered.

Illustrative of the current state of the art on tunneled epidural catheters is the Du Pen (TM) Long-Term Epidural Catheter commercially available form Davol Inc., Subsidiary of C. R. Bard, Inc. and reported in "A New Permanent Exteriorized Epidural Catheter for Narcotic Self-Administration to Control Cancer Pain" by Dr. Stuart L. DuPen et al, CANCER, Vol. 59, No. 5, Mar. 1, 1987, pp 986-993.

As stated therein, the new exteriorized epidural catheter consists of three pieces: (1) an epidural segment that is placed through a needle into the epidural space; (2) an exteriorized line equipped with an external luer connector and a subcutaneous Dacron cuff; and (3) a small splice segment to join the two catheter segments. Both the epidural and percutaneous lines are prepared from radiopague silicone rubber.

According to the protocol described collectively in the DuPen article and/or the Davol product literature, under local infiltration anesthesia, 7 cm paravertebral incision is made from the L-2 dorsal spine down to the paravertebral fascia, for needle placement and catheter splicing. A 14-gauge Hustead needle is then passed into the dorsal midline epidural space. With the aid of a guidewire, the epidural segment is advanced to the desired level within the epidural space. Epidural placement can be verified by ease of catheter passage, fluoroscopy and sensory blockade resulting from a 12-ml epidural dose of 2% lidocaine. Following placement of the epidural segment, the needle and guidewire are withdrawn and the proximal end of the catheter is trimmed to length.

The exteriorized line is tunneled from a subcostal location on the mid-nipple line (where it is easier to see and use) around to the lower end of the paravertebral incision. It is positioned with the Dacron cuff 5 cm internal (subcutaneous) from the exit site where the proximal end of the exteriorized line comes through the skin.

The small splice segment or catheter connector is then used to connect the two catheter ends together, using non-absorbable bridge ties to secure the catheter ends to the connector. To avoid damaging the catheter segments during this splicing operation, soft plastic sleeves provided with the "Du Pen" tray are slipped over the forceps tips for holding the ends. The splice segment is then secured to the supraspinus tissue to maintain a gentle curvature and to avoid kinking.

A conventional filter used for morphine injection, e.g. a Millex-OR 0.22 um filter unit from Millipore Corporation, is then attached to the luer connector and secured with tape. A dressing is then applied over the exit site and the filter may then be taped to the patient's skin.

The tunneled epidural catheter is then ready for connecting to the narcotic source.

While tunneled epidural catheters of the foregoing "two-piece" description provide a highly effective and efficacious means for relieving intractable pain originating below the cranial nerves, they nevertheless suffer from certain inherent disadvantages due to the manipulative steps required to assemble and prepare the catheter for drug administration into the epidural space, namely:

1. The catheter consists of two segments which have to be connected together at the paravertebral point where the epidural catheter component is introduced into the epidural space;

2. The dexterity involved in guiding the tunneler from the exit site to the paravertebral incision point and then bringing the described exteriorized line (proximal segment) in juxtaposition with the epidural segment for connection.

3. The necessity of trimming the segments to length for connection.

4. A third component, e.g. a connector, splicer or equivalent element is required to perfect the connection;

5. The procedural recommendation of suturing the connection to the supraspinous tissue to guard against any adverse movement of the distal end of the epidural segment positioned within the epidural space;

6. The fact that a relatively large paravertebral incision is required to make the necessary connection of the two catheter segments and to embed the resulting connection subcutaneously; and 7. The fact that during the surgical aspect of the catheterization, the recommended procedure requires fitting a pair of soft flexible sleeves provided in the catheter tray onto the forceps used to hold the catheter in order to avoid damage while performing the above steps;

As was heretofore mentioned, there is a recent trend for the responsibility for the treatment and control of pain to move from the surgeon to the anesthesiologist. The foregoing disadvantages are particularly apparent when one considers that by training, experience and personal inclination, the anesthesiologist is far more comfortable with a needle than he is with a scalpel and suture.

Stated simply, the task of the present invention is to provides a tunneled long-term epidural catheter which obviates the aforementioned disadvantages.

SUMMARY OF THE INVENTION

In accordance with the present invention the aforementioned objective is accomplished by providing an epidural catheter of one-piece construction extending subcutaneously from the paravertebral entry point to the exit site in combination with a protective reinforcement sleeve adapted to be positioned over the proximal section of the catheter extending above the exit site.

DESCRIPTION OF THE PREFERRED EMBODIMENTS

As was heretofore mentioned, the present invention is directed to an improved long-term tunneled epidural catheter for use in relieving intractable or chronic pain originating below the cranial nerves.

In accordance with this invention, the aforementioned disadvantages in the prior art two-piece tunneled epidural catheters is obviated in an elegant and highly efficacious manner by providing a one-piece epidural catheter which is tunneled from the paravertebral entry point where it is introduced into the epidural space to an exit site on the flank, the exteriorized proximal portion of the catheter being protected by a sleeve which is pre-attached at one end to a catheter connector, the free end of the sleeve extending over the catheter being inserted a short distance into the passage within the exit site provided by the tunneling step, as will be detailed with particularity hereinafter. The catheter connector is a component along with a liquid source connector component to provide an adapter for placing the catheter in liquid communication with the drug to be administered into the epidural space.

The arrangement of elements of the novel long-term epidural catheter system of the present invention may best be understood by reference to the accompanying drawings taken in conjunction with the following detailed description.

As shown therein, the exteriorized portion of the catheter system, i.e. that proximal portion extending through the exit site, comprises epidural catheter 10, sleeve 12 and catheter connector 18 to which the sleeve is pre-attached.

Catheter 10 has a lumen 11 through which a liquid drug may be transmitted for introduction into the epidural space.

Figure 1:
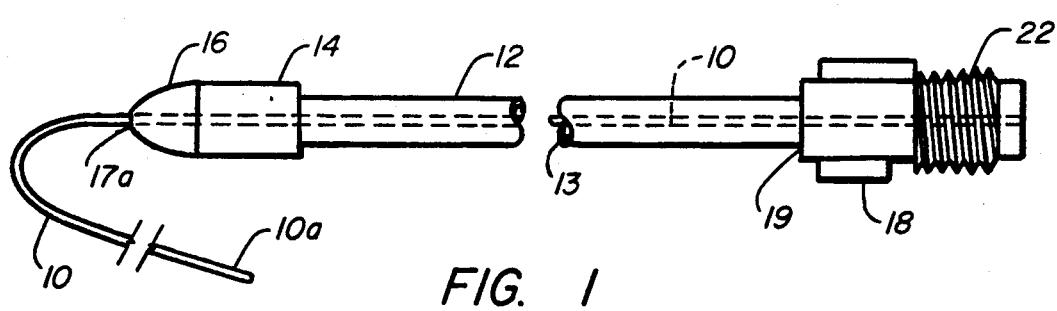
FIG. 1 is a fragmented longitudinal view of the preferred long-term epidural catheter of this invention illustrating the assembly of the component members: an epidural catheter inserted through a flexible reinforcement sleeve having an advancement tip and a cuff, the sleeve being pre-attached to an adapter for connecting the catheter to a liquid drug source.
Figure 2:
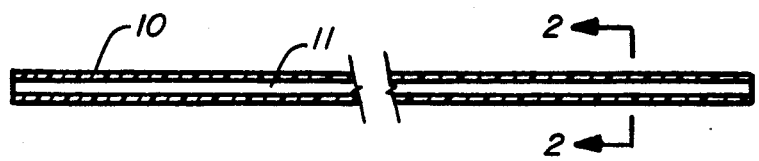
FIG. 2 is a longitudinal sectional view of the epidural catheter illustrating an internal lumen diameter in the catheter.
Figure 3:
FIG. 3 is an enlarged cross-sectional view of the epidural catheter taken along lines 2—2 of FIG. 2.
Figure 4:
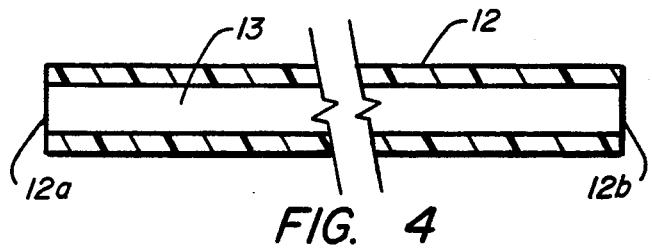
FIG. 4 is a longitudinal sectional view of the flexible reinforcement sleeve showing the inner and outer diameters thereof.
Figure 5:
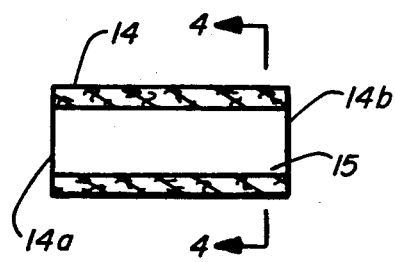
FIG. 5 is a sectional view of the cuff shown in FIG. 1.
Figure 6:
FIG. 6 is a cross-sectional view of the cuff taken along lines 4—4 of FIG. 5, illustrating its circular configuration.
Figure 7:
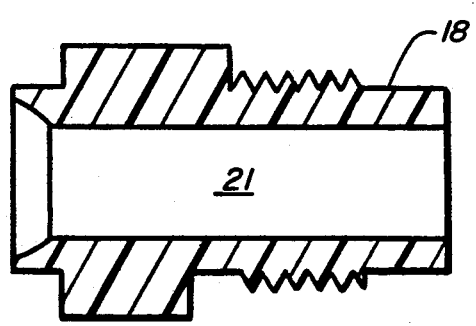
FIG. 7 is a longitudinal sectional view of a typical molded adapter component for securing the proximal ends of the catheter and sleeve.
Figure 8:
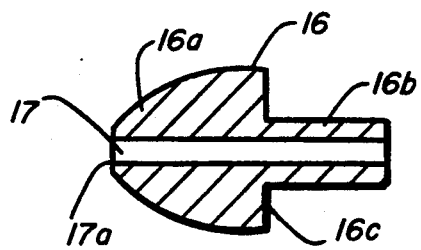
FIG. 8 is a longitudinal sectional view of the advancement tip illustrating its contoured body and extended shaft for attachment to the reinforcement sleeve.
Figure 9:
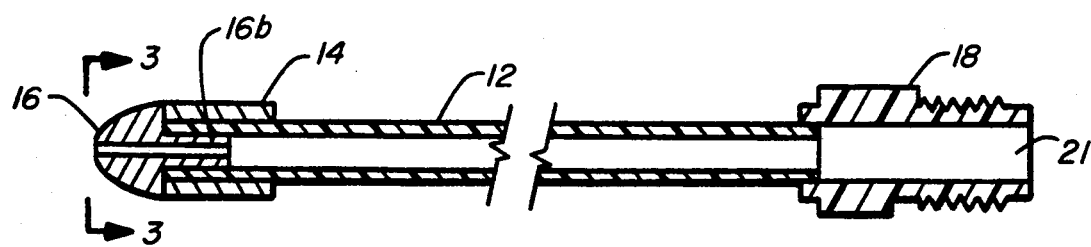
FIG. 9 is a longitudinal sectional view of the flexible reinforcement sleeve depicting the relationship of the pre-attached advancement tip, the cuff and adapter.
Figure 10:
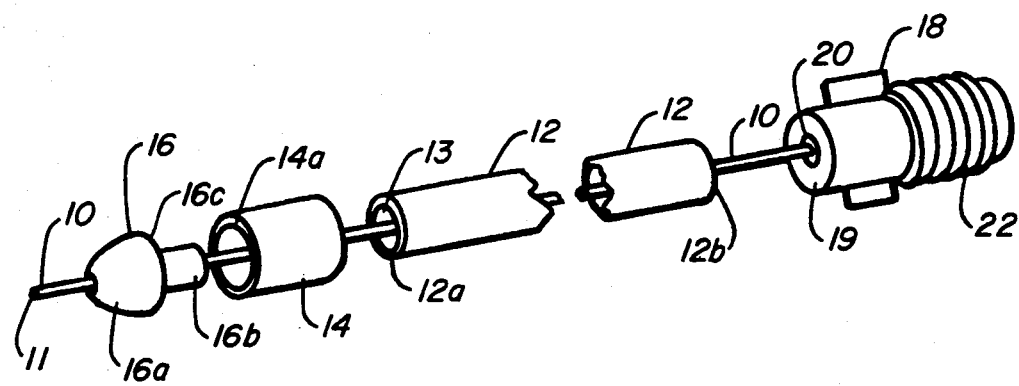
FIG. 10 is an exploded longitudinal view of the invention illustrating the assembly of the advancement tip, cuff, and the adapter to the sleeve, and the insertion of the catheter through the sleeve.
Figure 11:
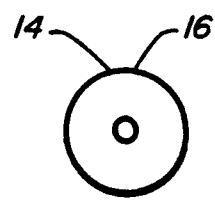
FIG. 11 is an end view of the preferred embodiment, taken along the line 3.3 of FIG. 9 illustrating that the advancement tip member and the cuff member are of the same diameter to facilitate movement of the cuff through subcutaneous tissue.

Sleeve 12 has distal and proximal ends 12a and 12b, respectively, between which extends a channel or hollow chamber 13 the inner diameter of which is greater than the outer diameter of the catheter 10 in order to accommodate positioning of the catheter within chamber 13, as seen, for example, in FIGS. 1 and 10. An advancement tip 16 is provided adjacent the distal end 12a of the sleeve in order to facilitate insertion of the sleeve beneath the skin at the exit site, as will be discussed hereinafter. As seen more clearly in FIGS. 8–10, tip 16 has a generally bullet-shaped leading end 16a tapering from a base 16c to optimize ease of penetration and a shaft 16b extending within the distal end 12a of the sleeve. As will be well understood, tip 16 is provided with a channel 17 communicating with an opening 17a at the leading end 16a to permit the catheter 10 to extend through the tip and then through chamber 13 of the sleeve. As seen, the base 16c of the bullet-shaped leading end of the tip is of greater outer diameter than that of the sleeve to minimize frictional resistance to entry of the sleeve within the passage beneath the skin created by the tunneling.

A cuff 14 of a suitable material such as a synthetic polyester, known as "DACRON" a trade-mark of the Dupont Company, located in Delaware, having leading and trailing ends 14a and 14b between which a hollow bore 15 extends is positioned on sleeve 12 with its leading end 14a abutting base 16c of the advancement tip, as best seen in FIG. 1. Cuff 14 and base 16c of the advancement tip have substantially the same diameter, whereby the skin tissue is caused to be opened enough by the tip to allow the cuff to follow easily into the tissue. When the cuff 14 is introduced into the tissue, it functions to encourage tissue ingrowth. Additionally, there is evidence that the cuff may tend to prevent infection by precluding passage of bacteria through the tunneled passageway and then down the external surface of the catheter.

As previously alluded to, the proximal or trailing end 12b of the shaft is pre-attached to the leading or distal end 19 of connector 18. Connector 18 has an opening 20 at its leading end extending into the hollow bore 21 within the connector for securing the catheter to the connector. Connector 18 also is shown to have external threads 22 at its proximal or trailing end adapted to mate with internal threads of a fluid source connector (not shown) in order to provide a fluid passageway extending from the fluid source into the epidural space for drug administration.

The particular adapter employed per se comprises no part of this invention. For purposes of further illustration, it may for instance comprise an adapter of the type described and claimed in U.S. Pat. No. 4,187,848 issued to Glenn N. Taylor and shown in FIG. 12.

As seen, the adapter consists of two separate body members which, for ease of reference, are designated as catheter connector 100 (corresponding to connector 18 in the previous figures) and a syringe connector 120. Both connectors have a longitudinally extending passageway for pumping narcotic from the syringe into the catheter.

Catheter connector 100 has an opening 140 at its distal end 160. A compressible plug 180 of elastomeric material having a longitudinally extending channel 200 is seated within a correspondingly shaped bore within connector 100 in a relatively uncompressed condition with channel 200 aligned with opening 140 to receive the proximal end of a catheter (not shown), as heretofore discussed.

Syringe connector 120 has a tapered port 220 at its proximal end 240 to receive the tip of a syringe (not shown). The proximal end 240 has luer lock flanges 250 and a female luer slip 260 adapted to receive the luer tip of the syringe so that the syringe may be releasably locked to connector 120. When employed in the practice of this invention to administer morphine, a filter unit (not shown) at the proximal end 240 is also required, as will be apparent to one skilled in the art.

Connector 100 has external threads 280 adjacent its proximal end which mate with internal threads 300 adjacent the distal end of syringe connector 120.

When the respective connectors are secured together, e.g. by rotating wings 320 on catheter connector 100, a compression collar 340 having an opening 360 (in liquid communication with channel 200 in external plug 180) compresses plug 180 to decrease the external dimensions (gap) of channel 200 to secure the catheter end in the adapter.

A preferred adapter for placing the catheter in liquid communication with the drug source is a one-piece adapter of the type described and claimed in the co-pending application of James R. Gross, Ser. No. 400,859 filed Aug. 30, 1989 and now U.S. Pat. No. 5,053,015.

Figure 15:
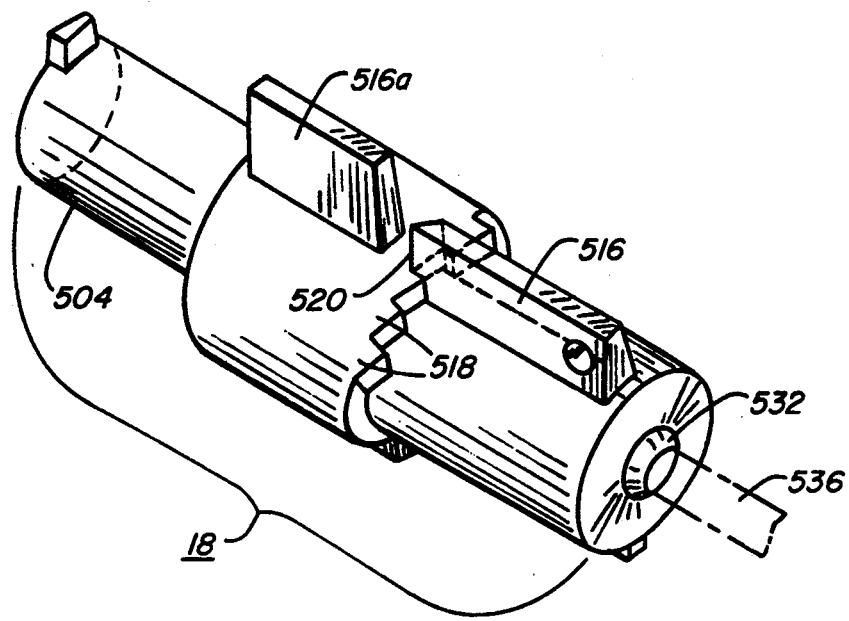
FIG. 15 is a perspective view illustrating the preferred adapter 18, as shown in FIG. 10 of the drawings to further illustrate how the catheter is secured by the adapter in conjunction with the combination of the sleeve and tip.
Figure 16:
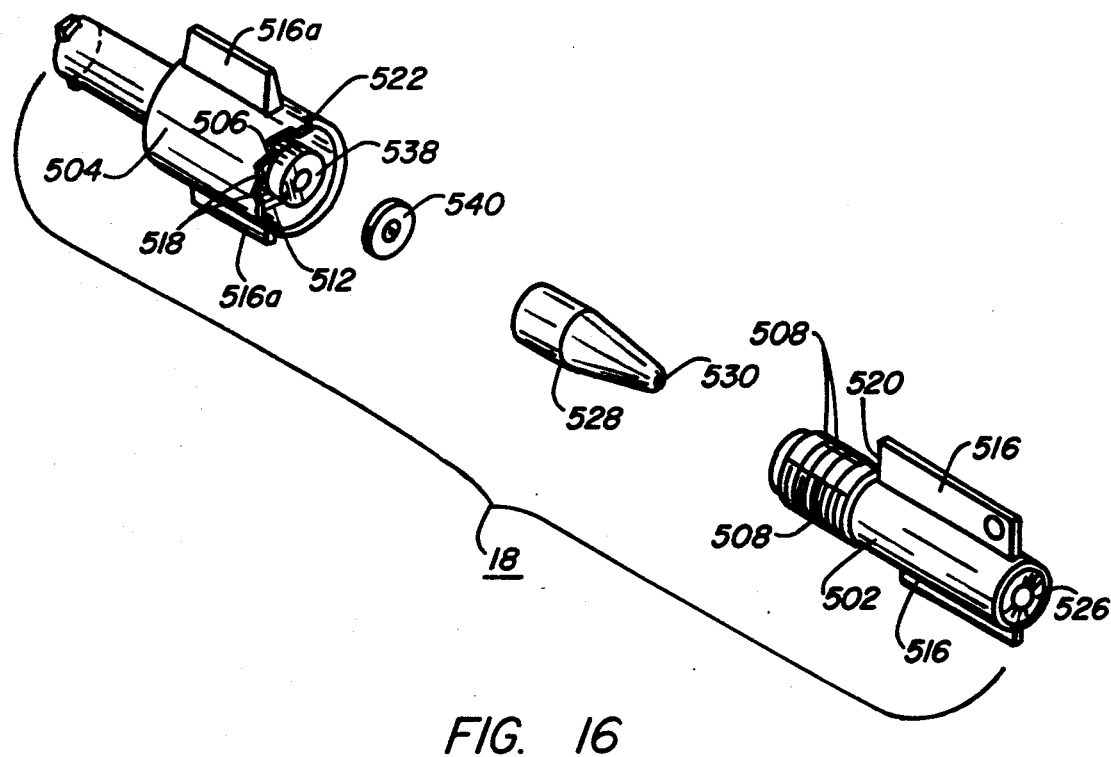
FIG. 16 is an exploded view of the adapter in FIG. 15.

As seen FIG. 15 and FIG. 16 illustrate the preferred adapter of this specification, as referenced in U.S. Pat. No. 5,053,015. As shown in FIG. 15 and 16 adapter 18 (FIG. 1 and FIG. 9 of the specification) has a catheter connector housing 502 and a syringe connector 504 secured in position as a unitary device by an external snap ring 506 which engages an internal snap ring (not shown) to prevent separation of the connectors. Catheter connector 502 has external threads 508 which mate with internal threads 512 of the syringe connector. By tightening or loosing the connection, e.g., by gripping one of the wings 516 or 516a and rotating the other, the connectors move longitudinally with respect to each other to either closed or open position. As seen an end of the syringe connector has teeth 518. When screwed together a locking wing 520 interferes with the ratchet type teeth 518 preventing the connectors from unscrewing or backing off. To prevent over tightening a full stop detent 522 is provided. An elongated plug 528 having a channel 530 is seated within connector 502. Plug 528 is positioned in relatively in an uncompressed condition with bore 530 aligned with opening 526 through which a catheter 536 may be inserted into bore 530. When the catheter 536 is so positioned, the wings 516 and 516a are rotated to place the adapter in the closed position with the locking wing edge 520 of the catheter connector abutting detent member 522. In the closed position, teeth 518 lock the two connectors together to prevent back-off. In this position compression collar 538 applies compressive force to the end of plug 528 causing it to compress longitudinally to narrow the gap of channel 530 and secure a catheter 536 in place. To prevent damage to the end of the channel a slop washer 540 is provided. As seen in FIG. 15 when the plug is compressed, the tip of the plug 528 extrudes through opening 526 providing a liquid-tight strain relief collar 532 for the catheter 536.

Figure 12:
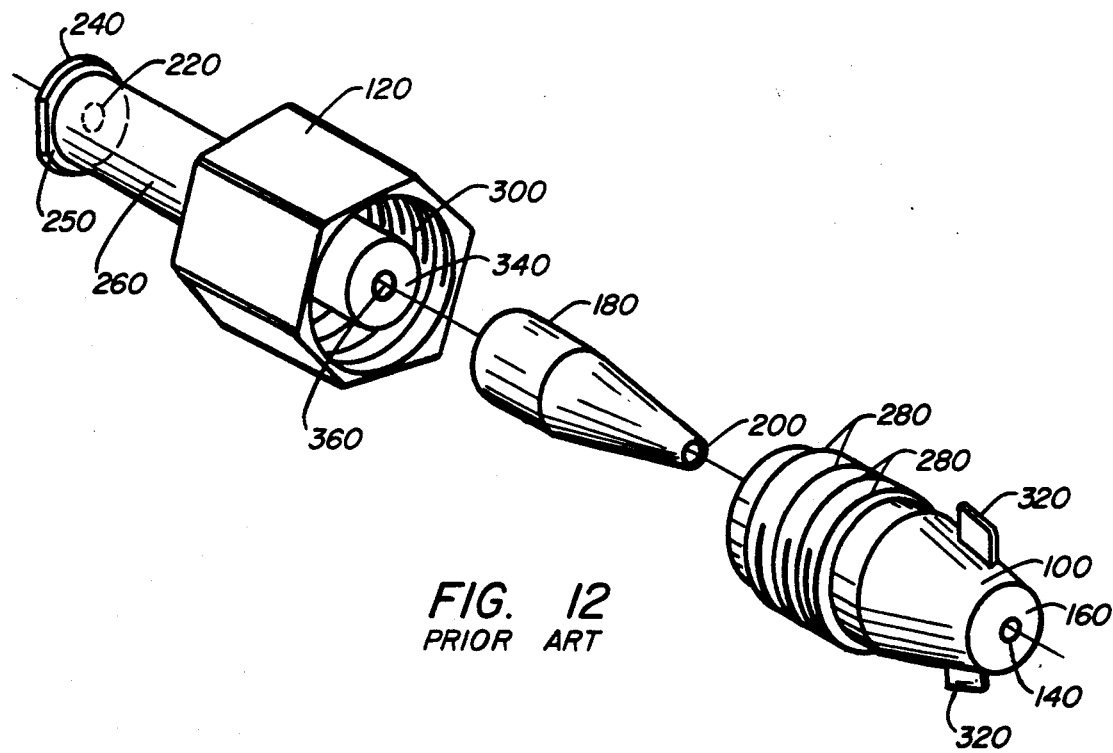
FIG. 12 is a fragmentary exploded elevational view of a prior art two-piece catheter adapter contemplated for use in connecting the epidural catheter of this invention to a liquid drug source.
Figure 13:
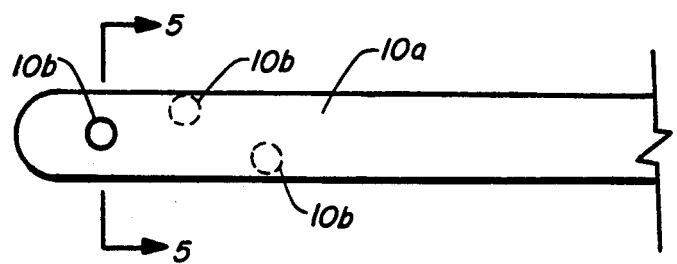
FIG. 13 is an enlarged fragmented longitudinal view of the proximal end of the catheter showing the ports for administering the narcotic into the body.
Figure 14:
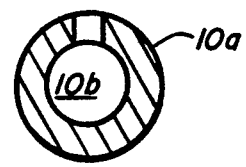
FIG. 14 is a cross-sectional view of the proximal end of the catheter taken along lines 5—5 of FIG. 13.

It will of course be understood that routine modifications may have to be made in the design of the adapter shown in FIG. 12 and/or that of the aforementioned application Ser. No. 400,859 in order to accommodate pre-attachment of the sleeve on the distal end of the adapter or the removable morphine filter/injection cap assembly at the proximal end. In any case, the adapter to be employed per se comprises no part of the present invention and any modifications in the illustrative adapters suggested above or the selection of alternative adapters will be a matter of choice within the expected judgement of the skilled worker in the light of the foregoing disclosure.

Catheter 10, which should in general be radiopaque for visibility on X-ray to confirm catheter placement, may be made of any of the materials heretofore employed in epidural catheter manufacture, e.g. a synthetic polymeric amide of the nylon family, "Teflon" (trademark of DuPont for polytetrafluoroethylene), polyurethane, silicone, etc., in which case it may typically possess an outer diameter of on the order of 1.3 mm (18 gauge), like the aforementioned "Du Pen" Long Term Epidural Catheter made of silicone rubber for introduction with the aid of a stylet through a 14-gauge Hustead needle.

However, in accordance with one embodiment of this invention, the catheter may be made of a polymeric composition which is characterized as being sufficiently stiff in the dry state during insertion to eliminate the need for a stylet, but which softens and swells on hydration in the body, which material will be on the order of 19-20 gauge and may be introduced with a smaller (17 gauge) needle.

Compositions of this general description are known in the art for preparing medical products such as body implants, tubular cannulas and the like which soften and swell when inserted into a living body and/or upon contact with an aqueous medium. By way of example of the state of the art pertaining thereto, mention may be made of the compositions disclosed in U.S. Pat. Nos. 4,883,699 and 4,911,691 issued to Anluk et al and U.S. Pat. Nos. 4,728,322 and 4,846,812 issued to Walker et al.

As stated in the aforementioned U.S. Pat. No. 4,911,691, for instance, such compositions may comprise a multiple phase polymer composition comprising:

(a) a first phase which comprises a substantially non-hydrophilic polymeric component; and (b) a second phase which comprises a hydrophilic polymeric component;

the composition (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

Preferably the non-hydrophilic polymeric component forms a continuous phase. The hydrophilic polymeric component can form a co-continuous phase with, or a dispersed phase in, the non-hydrophilic polymer phase.

The non-hydrophilic polymeric component comprises a polymer which does not substantially absorb or attract water. Preferably, the non-hydrophilic polymer is capable of absorbing in an amount of no more than about 30%, more preferably no more than about 15%, and most preferably no more than about 10%, by weight, based on the weight of the non-hydrophilic polymer.

The non-hydrophilic polymer can be for example, a polyurethane such an aliphatic polyurethane, a polyether polyurethane, a polyester polyurethane; and ethylene copolymer such as ethylene-vinyl acetate copolymer or ethylene-ethyl acrylate copolymer; a polyamide, in particular a polyamide of low crystallinity; aliphatic polyesters; or the like. A particularly preferred non-hydrophilic polymer is a polyurethane, especially an aliphatic polyurethane.

The hydrophilic polymer preferably is a polymer that absorbs at least about 50% water, more preferably about 100%, for example, at least about 150% by weight based on the weight of the hydrophilic polymer. The hydrophilic polymer preferably forms a hydrogel on absorption of water.

The hydrophilic polymer is preferably polyvinyl alcohol, poly(ethylene oxide), polypropylene oxide, poly(ethylene glycol) polypropylene glycol, polytetramethylene oxide, polyvinyl pyrolidene, polyacrylamide, polyhydroxy ethyl acrylate), poly(hydroxyethyl methacrylate), or the like.

Generally, the ratio of non-hydrophilic polymeric component to hydrophilic polymeric component is 0.65:1 to 9:1. Preferably the ratio of the polymeric component is 1:1 to 9:1.

The polymeric components are selected to provide a multiple phase system. Generally, the polymeric components each have a molecular weight of at least about 3,000 preferably at least about 5,000 and most preferably at least about 10,000.

By way of further illustration, the composition selected for use in the practice of this invention may have an inner diameter of 0.019 inch in the dry state and 0.027 inch when hydrated; and an outer diameter of 0.036 inch (20 gauge) in the dry state and 0.050 inch (18 gauge) when hydrated.

Catheters prepared from swellable materials such as those described above provide certain advantages in the preparation of epidural or subarachnoid catheters.

Such materials possess a stiffness comparable to Teflon when in the dry state, thereby permitting insertion without the need of a wire stylet. This in turn permits one to employ a smaller OD catheter, e.g. a 20 gauge which can be introduced with a 17 gauge needle. However, once in the body, the composition hydrates and softens comparable to silicone. The swelling which also occurs in a controlled reproducible manner when hydrated enlarges the catheter, e.g. to approximate the dimensions of the needle used to insert the catheter. In this manner, the swellable catheter will seal the puncture made by the needle, thereby sealing the ligamentum flavem and tending to eliminate any drug leakage out of the epidural space. The enlargement of the catheter after implantation may also serve to increase retention of the catheter in the tissue, thereby making it possible to retain the catheter in place without the need for any suturing. Moreover, the enlarged lumen size allows for higher flow rates and, consequently, improved drug delivery.

The reinforcement sleeve 12 should be made of a material which is characterized as being tough, durable and possessing good flexibility for optimum patient comfort. Preferably, it should also be clear for visualizing the epidural catheter within and possess low elongation so that the epidural catheter retained inside cannot be pulled out of the epidural space. As an example of a suitable material of this general description, mention may be made of commercially available nylon-braided polyurethane. It may, for example, be on the order of 18 inches in length and have an inner diameter of on the order of 0.071 inch and an outer diameter of around 0.142 inch (11 French).

Tip 16 may, for example, be made of stainless steel or a rigid plastic, the former being preferred. The outer diameter at its widest point (base 16c) may be slightly less than twice that of the sleeve, e.g. on the order of 0.245 inch. As will be appreciated, the outer diameter of shaft 16b should be such that it fits within the sleeve (as previously described) and the outer diameter of channel 17 must of course accommodate passage of the catheter.

Cuff 14 will be of no greater diameter than that of tip 16 and preferably will be of the same diameter. It may, for instance, be on the order of 0.375 inch in length. Preferably, it is retained in place on the sleeve by being bonded thereto. As heretofore mentioned, it may be made of a material such as Dacron felt which encourages tissue ingrowth.

It will of course be appreciated that the foregoing description of the materials and dimensions of the component parts of the epidural catheter of this invention are by way of illustration only and the scope of the invention is accordingly not limited thereto. Various other materials and sizes may be readily suggested to the skilled worker within the limits required for introducing the catheter with a needle into the epidural space.

The following description illustrates the preparation of the epidural catheter system of this invention for administration to a patient.

The epidural catheter is first threaded through a needle into the epidural space in per se known manner. With the needle still in place to avoid inadvertent damage to the catheter, a small incision is made with a scalpel extending cranially and caudally approximately 0.5–1.0 cm. All tissue is dissected away from the needle to allow the catheter to fall freely into the incision as the tunneler is later advanced. The epidural needle is then removed. If a wire stylet is used for insertion of the catheter, it is also removed.

With the aid of a tunneler, the catheter is then tunneled to the desired exit site, e.g. on the patient's flank. Tunnelers for use in this procedure are per se known in the art. In general, they fall into two basic categories: (1) a solid tunneler of metal or plastic in which one end of the catheter to be tunneled is slipped over the trailing end of the tunneler (the end opposed from the leading end having the cutting tip) and then dragged through the passageway created by the tunneler; or (2) a hollow tunneler open at the trailing end and having an opening in the cutting tip of sufficient diameter to permit passage of the catheter therethrough, in which case after the tunnel is made and with the tunneler still in place, the catheter may then be threaded through the opening in the tip and out the trailing end of the hollow tunneler.

While either type of these malleable tunnelers is quite satisfactory most of the time, each does nevertheless possess inherent properties which may adversely affect the tunneling step.

Since the solid tunneler functions by dragging the catheter behind it through the passageway created by tunneling, it follows that the catheter is dragged through the debris of host origin caused by the tunneler. This may, in turn, cause certain problems requiring the tunneling and, in some instances the insertion of the epidural catheter itself to be repeated. First, kinking of the catheter may be caused. Secondly, any undue or sudden resistance in the advancement of the catheter behind the tunneler may cause the catheter to slip off the trailing end of the tunneler. Finally, if the epidural catheter is the component to be tunneled (as will be the case with the catheter system of this invention) any such resistance may cause the distal end of the epidural catheter to become dislodged from its position within the epidural space. Such dislodgement may or may not require the catheter to be removed and re-introduced into the epidural space, depending upon the extent of the dislodgement.

The second type of tunneling device heretofore used, namely the hollow tunneler having an opening in the cutting tip, does not suffer from the inherent dangers noted above. However, it may instead cause different problems.

Since the cutting tip at the leading end of the tunneler has an opening permitting passage of the catheter therethrough, there is a tendency for flesh, blood and/or other debris from the tunneling to enter the hollow tunneler through this opening at the leading end. This in turn may at least partially clog up the passageway within the tunneler, notably at the leading end, thereby impairing threading the catheter therethrough and possibly causing kinking within the tunneler. Additionally, some of this debris of host origin may enter the leading end of the catheter, thus providing an environment for infection due to bacterial contamination.

Accordingly, the preferred tunneler for use in the practice of this invention is that described and claimed in Applicant's concurrently filed copending application, Ser. No. 703,320.

As disclosed therein, the tunneler consists of a malleable hollow shaft having a solid cutting tip releasably secured to one end thereof, e.g. by threading.

After tunneling and advancement of the tunneler through the exit site, the tip is then removed for passage of the catheter through the tunneler and then through the exit site.

Irrespective of the type of tunneler employed, after introducing the catheter into the epidural space as described about, the tunneler, being malleable, is then manually shaped to match the contour of the flank. The skin at the paravertebral incision is lifted and the shaped tunneler is introduced subcutaneously and then guided laterally toward the contemplated exit site on the flank.

When the tip of the tunneler has reached the desired exit point laterally, the tunneler is turned away from the patient, thereby forcing the cutting tip up against the skin. A scalpel is then used to cut down to expose the tip, after which the tunneler is advanced through the thus provided exit site.

When employing the novel tunneler described and claimed in the aforementioned copending application Ser. No. 703,320, following advancement of the leading end of the tunneler through the skin, the tunneler tip is removed and the catheter passed through the chamber or lumen within hollow shaft and out through end. The shaft is then removed through the exit site.

In any case, after the proximal end section of the catheter is exteriorized through the exit site, the protective sleeve 12 is advanced over the free proximal end of the catheter extending above the skin and down to the exit site. The skin is then lifted with forceps and the sleeve advanced through the exit site into the passage provided by the tunneler until the cuff 14 is approximately two inches beneath the skin.

The epidural catheter may then be trimmed to fit within the adapter 18 preattached to the sleeve and the adapter then moved to the closed position to secure the catheter.

Both the paramedial incision and ventral exit sites are then closed with suitable sutures and sterile dressings applied. After attaching a removable morphine filter-/injection cap assembly, a saline solution may be injected to confirm the catheter integrity.

The long-term epidural catheter is then ready to commence introducing narcotic into the epidural space on an as-needed dosage for pain management.

From the foregoing description it will thus be seen that the novel one-piece epidural catheter of this invention obviates all of the above-noted disadvantages of the prior two-piece systems in a simplified and elegant manner and additionally provides a protective covering on that portion of the catheter which is above the skin.

Since certain changes may be made without departing from the scope of the invention herein contemplated, it is to be expressly understood that the foregoing description, including the drawing, is by way of illustration and not be way of limitation and the invention is limited only as indicated in the appended claims.

What is claimed is:

1. An article adapted for use as a component part of a catheter system wherein a proximal section is exteriorized above the skin for connection to a liquid drug source for administration to a patient through the catheter, comprising, in combination:

a flexible sleeve having opposed proximal and distal ends defining a chamber within a sleeve having a diameter sufficiently great to permit passage of the catheter through the opposed ends of the sleeve, the sleeve having an advancement tip at its distal end adapted to facilitate advancement of the sleeve into a passage beneath the skin created by tunneling the catheter subcutaneously from the entry point where the distal end of the catheter is introduced into the body to an exit site where the proximal end is exteriorized for connection to an adapter, the advancement tip having a base section and a generally bullet-shaped leading end to which the top tapers from the base section to optimize ease of penetration, the base section having an outer diameter greater than the outer diameter of the sleeve, whereby to minimize frictional resistance to entry of the sleeve beneath the skin, the advancement tip having a channel extending therethrough for receiving the catheter for passage through the sleeve;

an adapter for placing the proximal end of the catheter in liquid communication with the drug source, the adapter having opposed proximal and distal ends;

a channel extending longitudinally between the adapter ends, an opening at the distal end of the adapter communicating with the adapter channel and through which the proximal end of the catheter can be inserted;

means for releasably securing the proximal end of the catheter within the opening and in liquid communication with the adapter channel;

and means for permanently attaching the proximal end of the sleeve to the distal end of the adapter with the sleeve chamber surrounding the opening in the adapter, whereby a catheter extending through the sleeve may be introduced into the adapter opening to receive liquid drug passing through the adapter channel for administration to the patient.

2. An article as defined in claim 1 wherein the advancement tip has a shaft extending from the base section to the trailing end of the advancement tip, the shaft extending within the distal end of the sleeve.

3. An article as defined in claim 1 wherein the advancement tip is made of a rigid material.

4. An article as defined in claim 3 wherein the material is metal.

5. An article as defined in claim 1 including a cuff positioned over the sleeve with its leading edge abutting the trailing end of the advancement tip.

6. An article as defined in claim 5 wherein the outer diameter of the cuff is substantially the same as the that of the base section of the advancement tip.

7. An article as defined in claim 6 wherein the cuff is made of a material which functions to encourage tissue growth when the cuff is inserted subcutaneously within the exit site for the catheter.

8. A long-term epidural catheter system for administration of a liquid drug through a catheter into a patient's epidural space comprising:

an epidural catheter having opposed distal and proximal ends, the distal end of the catheter being insertable through a patient's skin at a paravertebral entry point and then into the epidural space, the catheter being of a length sufficient to permit tunneling subcutaneously from the paravertebral entry point to a desired exit site away from the entry point where an exteriorized proximal section of the catheter can then extend through the exit site;

a flexible sleeve having opposed proximal and distal ends defining a chamber within the sleeve through which the exteriorized section of the catheter can extend, the sleeve having an advancement tip at its distal end adapted to facilitate advancement of the distal end of the sleeve beneath the skin at the exit site and into the passage beneath the skin created by tunneling the catheter to the exit site, the advancement tip having a leading end, a trailing end, a channel extending through the tip and a base section at the trailing end which tapers towards the leading end to optimize ease of penetration, the base section having an outer diameter greater than the outer diameter of the sleeve, whereby to minimize frictional resistance to entry of the sleeve beneath the skin;

an adapter for placing the proximal end of the catheter in liquid communication with the drug source, the adapter having opposed proximal and distal ends;

a channel extending longitudinally between the adapter ends;

an opening at the distal end of the adapter communicating with the adapted channel and through which the proximal end of the catheter extending through the proximal end of the sleeve can be introduced into the adapter;

means for releasably securing the proximal end of the catheter within the opening and in liquid communication with the adapted channel; and means permanently attaching the proximal end of the sleeve to the distal end of the adapter with the sleeve chamber surrounding the opening in the adapter, the proximal end of the catheter extending through the proximal end of the sleeve and then through the adapter opening and into the adapter where it is retained by the releasable securing means to receive liquid drug passing through the adapter channel for administration to the patient.

9. A catheter system as defined in claim 8 wherein the advancement tip has a shaft extending from the base section of the advancement tip, the shaft extending within the distal end of the sleeve.

10. A catheter system as defined in claim 8 wherein the advancement tip is made of a rigid material.

11. A catheter system as defined in claim 10 wherein the material is metal.

12. A catheter system as defined in claim 8 including a cuff positioned over the sleeve with its leading end abutting the trailing end of the advancement tip, the cuff being adapted for insertion beneath the skin of the patient at the exit site along with the distal end of the sleeve.

13. A catheter system as defined in claim 12 wherein the base section of the advancement tip and the cuff have outer diameters which are substantially the same.

14. A catheter system as defined in claim 13 wherein the cuff is made of a material which functions to encourage tissue growth when the cuff is inserted subcutaneously within the exit site for the catheter.

15. A catheter system as defined in claim 14 wherein the material is a synthetic polyester.

16. A catheter system as defined in claim 8 wherein the catheter is made from a polymeric composition which softens and swells on hydration in the body.

17. A catheter system as defined in claim 16 wherein the polymeric composition is characterized as being relatively stiff in the dry state such that the catheter can be inserted without the need of a stylet.

18. A catheter system as defined in claim 16 wherein the composition is a multiple phase polymer composition comprising: (a) a first phase which comprises a substantially non-hydrophilic polymeric component; and (b) a second phase which comprises a hydrophilic polymeric component.

19. A catheter system as defined in claim 18 wherein the non-hydrophilic polymeric component forms a continuous phase.

20. A catheter system as defined in claim 18 wherein the non-hydrophilic polymeric component comprises a polymer which does not substantially absorb or attract water.

21. A catheter system as defined in claim 20 wherein the hydrophilic polymer forms a hydrogel on absorption of water.

22. A catheter system as defined in claim 18 wherein the ratio of non-hydrophilic polymeric component to hydrophilic polymeric component is from about 0.65:1 to about 9:1.

* * * * *